US008048927B2

(12) United States Patent
Le Nestour (10) Patent No.: US 8,048,927 B2
(45) Date of Patent: *Nov. 1, 2011

(54) TREATMENT AND PREVENTION OF BENIGN BREAST DISEASE WITH 4-HYDROXY TAMOXIFEN

(75) Inventor: Elisabeth Le Nestour, Paris (FR)

(73) Assignee: Besins Healthcare Luxembourg, Luxembourg (LU)

( * ) Notice: Subject to any disclaimer, the term of this patent is extended or adjusted under 35 U.S.C. 154(b) by 64 days.

This patent is subject to a terminal disclaimer.

(21) Appl. No.: 12/397,487

(22) Filed: Mar. 4, 2009

(65) Prior Publication Data

US 2009/0203796 A1  Aug. 13, 2009

Related U.S. Application Data

(63) Continuation of application No. 10/805,528, filed on Mar. 22, 2004, now Pat. No. 7,507,769.

(51) Int. Cl.
*A01N 33/02* (2006.01)
*A01K 31/135* (2006.01)

(52) U.S. Cl. ........ 514/651; 514/344; 514/971; 424/449; 424/444

(58) Field of Classification Search .................. 514/651, 514/344, 971; 424/449, 444
See application file for complete search history.

(56) References Cited

U.S. PATENT DOCUMENTS

| | | | |
|---|---|---|---|
| 4,919,937 A | 4/1990 | Mauvais-Jarvis et al. | |
| 4,973,755 A | 11/1990 | Grafe et al. | |
| 5,045,553 A | 9/1991 | Ueda et al. | |
| 5,613,958 A | 3/1997 | Kochinke et al. | |
| 5,720,963 A | 2/1998 | Smith | |
| 5,904,930 A | 5/1999 | Fischer et al. | |
| 6,013,270 A | 1/2000 | Hargraves et al. | |
| 6,503,894 B1 | 1/2003 | Dudley et al. | |
| 6,632,841 B1 | 10/2003 | Af Ursin et al. | |
| 7,485,623 B2 | 2/2009 | Bua | |
| 7,507,769 B2 | 3/2009 | Nestour | |
| 7,704,516 B2 * | 4/2010 | Drouin et al. | 424/401 |
| 7,767,717 B2 | 8/2010 | Palumbo et al. | |
| 2001/0041718 A1 | 11/2001 | Thompson et al. | |
| 2003/0017539 A1 | 1/2003 | Glucksmann et al. | |
| 2003/0087885 A1 | 5/2003 | Masini-Eteve et al. | |
| 2003/0175329 A1 | 9/2003 | Azarnoff et al. | |
| 2004/0018991 A1 | 1/2004 | Schmidt et al. | |
| 2004/0086552 A1 | 5/2004 | Klokkers et al. | |
| 2004/0138314 A1 | 7/2004 | Bua | |
| 2005/0031695 A1 | 2/2005 | Rouanet et al. | |
| 2005/0032909 A1 | 2/2005 | Lignieres et al. | |
| 2005/0032910 A1 | 2/2005 | Palumbo et al. | |
| 2005/0158388 A1 | 7/2005 | Le Nestour et al. | |
| 2005/0208139 A1 | 9/2005 | Hilt et al. | |
| 2006/0105041 A1 | 5/2006 | Masini-Eteve | |
| 2009/0186944 A1 | 7/2009 | Rouanet et al. | |

FOREIGN PATENT DOCUMENTS

| | | |
|---|---|---|
| DE | 32 38 984 A1 | 5/1983 |
| DE | 38 36 862 A1 | 5/1990 |
| EP | 0 513 832 A1 | 11/1992 |
| EP | 1 579 856 A1 | 9/2005 |
| EP | 1 579 857 A1 | 9/2005 |
| WO | WO 99/33451 A2 | 7/1999 |
| WO | WO 01/43775 A2 | 6/2001 |
| WO | WO 2004/054557 A2 | 7/2004 |
| WO | WO 2004/054558 A2 | 7/2004 |
| WO | WO 2004/087123 | 10/2004 |

OTHER PUBLICATIONS

Wechter, MedlinePlus Medical Encyclopedia, "fibrocystic breast disease", Dec. 17, 2009 (3 pages).*
Kang et al. Arch Pathol. Lab Med 125(2001).*
J. Barrat et al., "Effet in vivo de l'administration locale de progestérone sur l'activité mitotique des galactophores humains", J. Gynecol. Obstet. Biol. Reprod. 19: 269-274 1990.
Bronaugh & Maibach, "Percutaneous Absorption Drugs-Cosmetics-Mechanisms-Methodology", Marcel Dekker Inc., New York, 1999.
Philip Carthew et al., "Cumulative exposure to tamoxifen: DNA adducts and liver cancer in the rat", Arch Toxicol (2001) 75: 375-380.
Gerard Chetrite et al., "Effect of Promegestone, Tamoxifen, 4-Hydroxytamoxifen and ICI 164,384 on the Oestrone Sulphatase Activity of Human Breast Cancer Cells", Anticancer Research 13: 931-934 (1993).
Eric C. Dietze et al., "Tamoxifen but Not 4-Hydroxytamoxifen Initiates Apoptosis in p53(−) Normal Human Mammary Epithelial Cells by Inducing Mitochondrial Depolarization", The Journal of Biological Chemistry vol. 276, No. 7, Issue of Feb. 16, 2001, pp. 5384-5394.
Ian S. Fentiman, "Tamoxifen and Mastalgia an Emerging Indication", Drugs, vol. 32, No. 6, Dec. 1986, pp. 477-480.
I.S. Fentiman et al., "Dosage and duration of tamoxifen treatment for mastalgia: a controlled trial", Br. J. Surg. Sep. 1988, vol. 75, No. 9, pp. 845-846.
I.S. Fentiman et al., "Studies of tamoxifen in women with mastalgia*", The British Journal of Clinical Practice, Supplement 68, vol. 43, No. 11, Nov. 1989, pp. 34-36. N. Giambiagi et al., "Immunological Differences Between the Estradiol-, Tamxifen- and 4-Hydroxy-Tamoxifen-Estrogen Receptor Complexes Detected by Two Monoclonal Antibodies", J. Steroid Biochem. vol. 30, No. 1-6, pp. 213-217, 1988.
V. Craig Jordan et al., "Metabolites of tamoxifen in animals and man: identification, pharmacology, and significance", Breast Cancer Research and Treatment, 2, pp. 123-138.
George G.J.M. Kuiper et al., "Comparison of the Ligand Binding Specificity and Transcript Tissue Distribution of Estrogen Receptors α and β", Endocrinology, vol. 138, No. 3, 1997, pp. 863-870.
Frédérique Kuttenn et al., "Médecine Et Thérapeutique", C.R. Acad. Sc. Paris, , Série III, No. 12, 1985, 300:457-461.

(Continued)

*Primary Examiner* — Brandon Fetterolf
*Assistant Examiner* — Shirley V Gembeh
(74) *Attorney, Agent, or Firm* — Foley & Lardner LLP (57) ABSTRACT

The present invention provides methods for treating and preventing benign breast disease by administering 4-hydroxy tamoxifen to a patient. When percutaneously administered to a patient's breasts, 4-hydroxy tamoxifen concentrates locally, and exerts an anti-estrogenic effect. In patients with benign breast disease, this effect induces disease regression. In patients at risk for developing breast cancer, the anti-estrogenic effect prevents formation of benign breast conditions that can lead to cancer.

16 Claims, 2 Drawing Sheets

OTHER PUBLICATIONS

Catherine Malet et al., "Tamoxifen and Hydroxytamoxifen Isomers *versus* Estradiol Effects on Normal Human Breast Cells in Culture", Cancer Research, vol. 48, No. 24, Dec. 15, 1988, pp. 7193-7199.

Pierre Mauvais-Jarvis et al., "trans-4-Hydroxytamoxifen Concentration and Metabolism after Local Percutaneous Adminstration to Human Breast", Cancer Research, vol. 46, Mar. 1986, pp. 1521-1525.

Henri Pujol et al., "Phase I Study of percutaneous 4-hydroxy-tamoxifen with analyses of 4-hydroxy-tamoxifen concentrations in breast cancer and normal breast tissue", Cancer Chemother. Pharmacol., 36:493-498 (1995).

David W. Robertson et al., "Synthesis of the *E* and *Z* Isomers of the Antiestrogen Tamoxifen and Its Metabolite, Hydroxytamoxifen, in Tritium-Labeled Form", J. Org. Chem., 1982, vol. 47, No. 12, pp. 2387-2393.

David W. Robertson et al., "Tamoxifen Antiestrogens, A Comparison of the Activity, Pharmacokinetics, and Metabolic Activation of the *CIS* and *Trans* Isomers of Tamoxifen" Journal of Steroid Biochemistry, vol. 16, pp. 1-13, (1982).

Fabrice Sauvez et al., "Cutaneously applied 4-hydroxytamoxifen is not carcinogenic in female rats", Carcinogenesis vol. 20, No. 5, pp. 843-850 1999.

John N. Wolfe MD, "Risk for Breast Cancer Development Determined by Mammographic Parenchymal Pattern", Cancer, May 1976, vol. 37, No. 5, pp. 2486-2492.

Carol A. Bodian Dr.P.H., et al., "Prognostic Significance of Benign Proliferative Breast Disease", Cancer, Jun. 15, 1993, vol. 71, No. 12, pp. 3896-3907.

Christine L. Carter et al., "A Prospective Study of the Development of Breast Cancer in 16,692 Women with Benign Breast Disease", American Journal of Epidemiology, vol. 128, No. 3, Sep. 1988, pp. 467-477.

William D. Dupont Ph.D. et al., "Risk Factors for Breast Cancer in Women With Proliferative Breast Disease", The New England Journal of Medicine, vol. 312, No. 3, Jan. 1985, pp. 146-151.

William D. Dupont Ph.D. et al., "Long-Term Risk of Breast Cancer in Women with Fibroadenoma", The New England Journal of Medicine, vol. 331, No. 1, Jul. 1994, pp. 10-15.

Patrick L. Fitzgibbons, MD. et al., "Benign Breast Changes and the Risk for Subsequent Breast Cancer", Arch. Pathol. Lab. Med. vol. 122, Dec. 1998, pp. 1053-1055.

Stanley G. Korenman et al., "Estradiol Radioimmunoassay Without Chromatography: Procedure, Validation and Normal Values", J. Clin. Endocrinol. Metab. 38, pp. 718-720, 1974.

Nancy Krieger et al., "Risk of Breast Cancer after Benign Breast Diseases Variation by Histologic Type, Degree of Atypia, Age at Biopsy, and Length of Follow Up", American Journal of Epidemiology, vol. 135, No. 6, pp. 619-631, Mar. 1992.

Kyung-Hoon Lee et al., "Quantification of tamoxifen and three metabolites in plasma by high-performance liquid chromatography with fluorescence detection: application to a clinical trial", Journal of Chromatography B., 791 (2003), pp. 245-253.

Mizuki Nishino et al., "Effects of Tamoxifen on Hepatic Fat Content and the Development of Hepatic Steatosis in Patients with Breast Cancer; High Frequency of Involvement and Rapid Reversal After Completion of TAmoxifen Therapy", AJR: 180, Jan. 2003, pp. 129-134.

Lawrence H. Block PhD "Epidermal and Transdermal Drug Delivery", The Science and Practice of Pharmacy, Medicated Topicals, pp. 836-857 (2000).

Asher Shushan MD et al., "Ovarian cysts in premenopausal and postmenopausal tamoxifen-treated women with breast cancer", Am. J. Obstet Gynecol. Jan. 1996, pp. 141-144.

Elizabeth Tan-Chiu et al., "Effects of Tamoxifen on Benign Breast Disease in Women at High Risk for Breast Cancer", Journal of the National Cancer Institute, vol. 95, No. 4, Feb. 19, 2003, pp. 302-307.

Yasuo Hozimi et al., "Effect of Tamoxifen on Serum Lipid Metabolism", Journal of Clinical Endocrinology and Metabolism, vol. 83, No. 5, pp. 1633-1635.

European Search Report of EP 04 29 0761.

Pierre Mauvais-Jarvis et al., "trans 4-Hydroxytamoxifen Concentration and Metabolism after Local Percutaneous Administration to Human Breast", Cancer Research vol. 46, No. 3, pp. 1521-1525, Mar. 1986.

I. Simony-Lafontaine et al., "Neoadjuvant percutaneous-4-hydroxytamoxifen decreases breast cancer cell proliferation: A prospective randomized image analysis Study", Analytical Cellular Pathology, Elsevier Science, Amsterdam, NL., vol. 25, No. 5-6, Oct. 1, 2003, pp. 258-259, XP009030125 ISSN: 0921-8912 *Abstract.

F. Kuttenn et al., "Basis for percutaneous administration of antiestrogens in breast pathology", Contraception Fertilite Sexualite, vol. 19, No. 2, 1991, pp. 165-171.

International Search Report of PCT/EP2005/003286.

Beers et al., The Merck Manual of Diagnosis and Therapy, Seventeenth Edition, Merck Research Laboratories, (1999), Chapter 242, pp. 1973-1974.

Tan-Chiu et al., *J. Nat. Cancer Inst.*, 2003, vol. 95(4), pp. 302-207.

Ader et al., "Prevalence and Impact of Cyclic Mastalgia in a United States Clinic-Based Sample," Am. J. Obstet. Gynecol. 177:126-132 (1997).

Alberti et al., "In Vivo Assessment of Enhanced Topical Delivery of Terbinafine to Human Stratum Corneum," J. of Controlled Release 71:319-327 (2001).

Callantine et al., "Micronized 17 β-Estradiol for Oral Estrogen Therapy in Menopausal Women," Obstretrics & Gynecology 46(1):37-41 (Jul. 1975).

Friend et al., "Simple Alkyl Esters as Skin Permeation Enhancers," Journal of Controlled Release, 9(1):33-41 (Jun. 1989) (Abstract Only).

Giambiagi et al., "Immunological Differences Between the Estradiol-, Tamoxifen- and 4-Hydroxy-Tamoxifen-Estrogen Receptor Complexes Detected by Two Monoclonal Antibodies," J. Steroid Biochem, 30(1-6):213-217 (1988).

A. Gorins et al., "A French Double-Blind Crossover Study (Danazol Versus Placebo) in the Treatment of Severe Fibrocystic Breast Disease," Eur. J. Gynaec. Oncol. 2:85-89 (1984).

S.J. Graham, Ph.D., et al., "Changes in Fibroglandular Volume and Water Content of Breast Tissue During the Menstrual Cycle Observed by MR Imaging at 1.5 T," JMRI 5:695-701 (1995).

IBIS Investigators, "First Results from the International Breast Cancer Intervention Study (IBIS-I): a Randomised Prevention Trial," The Lancet 360:817-824 (Sep. 14, 2002).

R.E. Mansel et al., "A Double Blind Trial of a Prolactin Inhibitor Bromocriptine in Painful Benign Breast Disease," Br. J. Surg. 65:724-737 (1978).

P. Mauvais-Jarvis, "Le Traitement Hormonal des Mastopathies Bénignes," Bull Cancer 78:365-371 (1991).

P. Mauvais-Jarvis, "Mastodynia and Fibrocystic Disease," Current Therapy in Endocrinology and Metabolism 3:280-284 (1988).

P. Mauvais-Jarvis et al., "Hormonal Therapy of Benign Breast Disease," Senologie et Pathologie Mammaire. 4éme Congrés International, Paris, pp. 128-132 (Sep. 1-4, 1986).

C.S. Murphy et al., Structure-Function Relationships of Hydroxylated Metabolites of Tamoxifen that Control the Proliferation of Estrogen-Responsive T47D Breast Cancer Cells in Vitro, Molecular Pharmacology 38:737-743 (1990).

Ruland et al., "Influence of Various Penetration Enhancers on the in Vitro Permeation of Amino Acids Across Hairless Mouse Skin," International Journal of Pharmaceutics, 85(1-3):7-17 (Sep. 1992).

Sambrook et al., "Ultrasonic Doppler Study of the Hormonal Response of Blood Flow in the Normal Human Breast," Ultrasound in Med & Biol., 13(3):121-129 (1987).

Santoyo et al., "Penetration Enhancer Effects on the in Vitro Percutaneous Absorption of Piroxicam Through Rat Skin," International Journal of Pharmaceutics, 117:219-224 (1995).

Notice of Allowance dated Jun. 13, 2008 from U.S. Appl. No. 10/734,638 (7 pgs.).

Final Office Action dated Dec. 11, 2007 from U.S. Appl. No. 10/734,638 (20 pgs.).

Final Office Action dated Mar. 13, 2007 from U.S. Appl. No. 10/734,638 (21 pgs.).

Final Office Action dated Oct. 2, 2006 from U.S. Appl. No. 10/734,638 (15 pgs.).

Non-Final Office Action dated May 5, 2006 from U.S. Appl. No. 10/734,638 (22 pgs.).
Final Office Action dated May 29, 2008 from U.S. Appl. No. 10/734,640 (19 pgs.).
Non-Final Office Action dated Aug. 23, 2007 from U.S. Appl. No. 10/734,640 (14 pgs.).
Non-Final Office Action dated Mar. 12, 2007 from U.S. Appl. No. 10/734,640 (9 pgs.).
Notice of Allowance dated Jun. 24, 2008 from U.S. Appl. No. 10/734,644 (6 pgs.).
Non-Final Office Action dated Oct. 4, 2007 from U.S. Appl. No. 10/734,644 (12 pgs.).
Non-Final Office Action dated Apr. 10, 2007 from U.S. Appl. No. 10/734,644 (11 pgs.).
Final Office Action dated Feb. 24, 2006 from U.S. Appl. No. 10/734,644 (10 pgs.).
Non-Final Office Action dated Aug. 23, 2005 from U.S. Appl. No. 10/734,644 (9 pgs.).
Non-Final Office Action dated Jun. 18, 2008 from U.S. Appl. No. 10/858,399 (12 pgs.).
Non-Final Office Action dated Nov. 1, 2007 from U.S. Appl. No. 10/858,399 (15 pgs.).
Final Office Action dated Jul. 9, 2008 from U.S. Appl. No. 11/009,390 (16 pgs.).
Non-Final Office Action dated Nov. 28, 2007 from U.S. Appl. No. 11/009,390 (15 pgs.).
Malet et al., "Effect of 4-Hydroxytamoxifen Isomers on Growth and Ultrastructural Aspects of Normal Human Breast Epithelial (HBE) Cells in Culture," Journal of Steroid Biochemistry & Molecular Biology 82:289-296 (2002).
Fournier et al., "Hormonal and Non-Hormonal Medical Therapy of Benign Breast Disease," *Horm. Res.*, vol. 32, Supp. 1, pp. 28-31, 1989.
Wijayaratne et al., "Comparative Analyses of Mechanistic Differences Among Antiestrogens," *Endocrinolgy*, vol. 140, No. 12, pp. 5828-5840, 1999.
Yu et al., Simple and Efficient Production of (Z)-4-Hydroxytamoxifen, a Potent Estrogen Receptor Modulator, *J. Org. Chem.*, vol. 68, pp. 9489-9491, 2003.
Notice of Allowance issued on Dec. 22, 2009 in U.S. Appl. No. 10/734,638 (US 7,704,516.
Office Action issued on Nov. 12, 2009 in U.S. Appl. No. 10/734,638 (US 7,704,516).
Office Action issued on Jan. 6, 2009 in U.S. Appl. No. 10/734,638 (US 7,704,516).
Office Action issued on Jan. 16, 2007 in U.S. Appl. No. 10/734,638 (US 7,704,516).
Notice of Allowance issued on Feb. 2, 2010 in U.S. Appl. No. 10/734,640 (US 2005/0032909).
Office Action issued on Aug. 4, 2009 in U.S. Appl. No. 10/734,640 (US 2005/0032909).
Office Action issued on Dec. 16, 2008 in U.S. Appl. No. 10/734,640 (US 2005/0032909).
Office Action issued on Jul. 7, 2006 in U.S. Appl. No. 10/734,644 (US 7,485,623).
Office Action issued on Nov. 4, 2010 in U.S. Appl. No. 10/805,530 (US 2005/0208139).
Office Action issued on Feb. 2, 2010 in U.S. Appl. No. 10/805,530 (US 2005/0208139).
Office Action issued on Sep. 15, 2009 in U.S. Appl. No. 10/805,530 (US 2005/0208139).
Office Action issued on Sep. 3, 2008 in U.S. Appl. No. 10/805,530 (US 2005/0208139).
Notice of Allowance issued on Jan. 20, 2010 in U.S. Appl. No. 10/858,399 (US 7,767,717).
Office Action issued on Aug. 18, 2009 in U.S. Appl. No. 10/858,399 (US 7,767,717).
Office Action issued on May 19, 2009 in U.S. Appl. No. 10/858,399 (US 7,767,717).
Office Action issued on Feb. 5, 2009 in U.S. Appl. No. 10/858,399 (US 7,767,717).
Office Action issued on Aug. 24, 2010 in U.S. Appl. No. 11/009,390 (US 2005/0158388).
Office Action issued on Mar. 30, 2010 in U.S. Appl. No. 11/009,390 (US 2005/0158388).
Office Action issued on Nov. 9, 2009 in U.S. Appl. No. 11/009,390 (US 2005/0158388).
Office Action issued on Jan. 23, 2009 in U.S. Appl. No. 11/009,390 (US 2005/0158388).
Office Action issued on Apr. 9, 2010 in U.S. Appl. No. 11/249,122 (US 2006/0105041).
Office Action issued on May 5, 2009 in U.S. Appl. No. 11/249,122 (US 2006/0105041).
Office Action issued on Aug. 25, 2010 in U.S. Appl. No. 12/353,890 (US 2009/0186944).
Notice of Allowance issued on Nov. 7, 2010 in U.S. Appl. No. 10/805,528 (US 7,507,769).
Office Action issued on Feb. 8, 2008 in U.S. Appl. No. 10/805,528 (US 7,507,769).
Office Action issued on Feb. 9, 2007 in U.S. Appl. No. 10/805,528 (US 7,507,769).
Office Action issued on Jul. 17, 2006 in U.S. Appl. No. 10/805,528 (US 7,507,769).
Office Action issued on Nov. 2, 2005 in U.S. Appl. No. 10/805,528 (US 7,507,769).

* cited by examiner

FIGURE 1: Representation of Tamoxifen Metabolism

Figure 2: Mean ± SD Plasma Concentration of 4-hydroxy tamoxifen in Healthy Women Following Last Cutaneous Administration (Day 25 of the Second Cycle)

TREATMENT AND PREVENTION OF BENIGN BREAST DISEASE WITH 4-HYDROXY TAMOXIFEN

CROSS REFERENCE TO RELATED APPLICATIONS

This application is a continuation of U.S. application Ser. No. 10/805,528, filed Mar. 22, 2004, which is incorporated herein by reference in its entirety.

BACKGROUND OF THE INVENTION

The present invention relates to the treatment and prevention of benign breast diseases with 4-hydroxy tamoxifen (4-OHT).

Benign breast disease refers to a constellation of common non-malignant aberrations in breast tissue. These aberrations include numerous lesions that have well-defined histological characteristics, and can be classified as proliferative or non-proliferative. Notable examples include adenosis, cysts, duct ectasia, fibroadenoma, fibrocystic disease, fibrosis, hyperplasia and metaplasia. Because benign breast disease is estrogen-related, the affected population is mainly adult premenopausal women. In this population, benign breast disease can interfere with childbearing and contraception, and current treatment options can adversely affect patient quality of life.

Although benign breast disease rarely poses an immediate threat to a patient's health, it often causes persistent emotional anxiety and physical pain. In particular, benign lesions must be histologically evaluated to distinguish them from breast cancer. Such evaluations are expensive, time consuming, frequently invasive (e.g., repeated needle aspirations, biopsies and ductal lavage) and painful, and submit a patient to high amounts of emotional stress.

Additionally, numerous studies have demonstrated that women with a history of benign breast disease have an increased breast cancer risk (Dupont, 1985; Fitzgibbons, 1998; Carter 1988; and Krieger, 1992). The level of risk varies by type of benign lesion. For example, fibroadenoma increases the risk of invasive breast cancer 2.2 fold, adenosis increases the risk 3.7 fold, duct atypia increases the risk 3.9 fold and atypical hyperplasia increases the risk 5.3 fold (Dupont, 1985; Bodian, 1993; Dupont, 1994). The risk for developing breast cancer further increases when the presence of benign breast disease is combined with a family history of breast cancer. For instance, atypia combined with a family history of breast cancer increases a patient's risk for developing breast cancer 11 fold (Dupont, 1985).

Administration of the breast cancer drug tamoxifen significantly reduces the risk that a patient will develop benign breast disease (Tan-Chiu, 2003). In this regard, tamoxifen works by competitively binding to estrogen receptors, thereby blocking the effects of estrogen on breast cells. Overall, tamoxifen reduces the risk of developing benign breast disease by 28%, but the reduction varies according to disease type. One recent study reported statistically significant decreases of 41% for adenosis, 34% for cyst, 28% for duct ectasia, 33% for fibrocystic disease, 40% for hyperplasia and 49% for metaplasia. For women under 50, the administration of tamoxifen reduced by 41% the need for breast biopsies. The psychological and economic implications of such reductions are enormous.

In spite of its benefits, tamoxifen has significant drawbacks. Its action potentially impacts on every estrogen receptor-bearing cell in the body, and, as both an agonist and antagonist, tamoxifen provokes a wide range of systemic effects. These effects increase the risk of endometrial cancer and sarcoma, endometrial hyperplasia and polyps, ovarian cysts, deep vein thrombosis and pulmonary embolism, changes in liver enzyme levels and hepatic steatosis, hyperlipidemia, and ocular toxicities, including cataracts (Shushan, 1996; Nishino, 2003; Hoxumi, 1988). Intake of oral tamoxifen precludes pregnancy, even two months after stopping treatment, and precludes the use of hormonal contraception. Additionally, patients treated with oral tamoxifen report having hot flashes, vaginal discharge, depression, amenorrhea, and nausea (Ibis, 2002; Fentiman 1986, 1988, 1989).

A strong need, therefore, still exists for methods to treat and to prevent benign breast diseases without provoking significant adverse systemic side effects, particularly in the premenopausal population.

SUMMARY OF THE INVENTION

The present invention includes a method of treating benign breast disease by administering 4-hydroxy tamoxifen. This treatment approach preferably is implemented topically, resulting in lower plasma drug levels than those from oral tamoxifen.

The present invention also includes a method of preventing benign breast disease by administering 4-hydroxy tamoxifen. As with the treatment approach, the prophylactic approach also preferably is implemented topically.

For purposes of prophylaxis or treatment, 4-hydroxy tamoxifen may be administered by any means that delivers it to estrogen receptor-bearing cells in vivo. As noted, it is preferable that the administration be done percutaneously (topically), to avoid the first-pass effect and related liver metabolism of the 4-hydroxy tamoxifen. For percutaneous administration, 4-hydroxy tamoxifen may be applied to any skin surface. Application to the breasts is advantageous because 4-hydroxy tamoxifen tends to concentrate in local subcutaneous tissues with estrogen receptors when administered percutaneously.

A broad range of topical formulations are suitable for performing the invention, but hydroalcoholic solutions and hydroalcoholic gels are preferred. The concentration of 4-hydroxy tamoxifen in these formulations may vary, but a dose should result in local 4-hydroxy tamoxifen tissue concentrations that effectively oppose estrogenic driven effects.

DETAILED DESCRIPTION OF THE PREFERRED EMBODIMENTS

An important aspect of the present invention is the surprising discovery that 4-hydroxy tamoxifen, when administered percutaneously, is effective for both treating and preventing benign breast diseases. Moreover, percutaneously administered 4-hydroxy tamoxifen results in lower plasma levels of the drug (4-OHT) than the standard dose of oral tamoxifen and in nearly none of the other metabolites found after oral tamoxifen intake, which should translate to fewer adverse side effects (Lee, 2003). Accordingly, percutaneous 4-hydroxy tamoxifen is an alternative to tamoxifen for both treatment and prophylaxis in this context.

The compound 4-hydroxy tamoxifen, or 1-[4-(2-N-dimethylaminoethoxy)phenyl]-1-(4-hydroxyphenyl)-2-phenylbut-1-ene, constitutes an active metabolite of the well characterized anti-estrogen compound, tamoxifen. Due to the presence of a double bond between two carbon atoms, 4-hydroxy tamoxifen exists in two stereoisomeric forms. According to the medical and biochemical literature, isomeric forms of 4-hydroxy tamoxifen are commonly designated as cis and trans isomers. From a purely chemical perspective, however, this designation is not strictly accurate because each double bonded carbon atom does not contain an identical chemical group. Therefore, it is more appropriate to refer to the isomers as E (the so-called cis form) and Z (the so-called trans form) configurations. Both the E and Z isomers of 4-hydroxy tamoxifen, either alone or in combination, are useful according to the present invention. The Z isomer is preferred, however, because it is more active than the E isomer.

4-Hydroxy tamoxifen acts as a selective estrogen receptor modulator (SERM) that exhibits tissue-specificity for estrogen receptive tissues. In breast tissue, it functions as an estrogen antagonist. Studies have shown that 4-hydroxy tamoxifen can regulate the transcriptional activity of estrogen-related receptors, which may contribute to its tissue-specific activity. In vitro, 4-hydroxy tamoxifen exhibits more potency than tamoxifen, as measured by binding affinity to estrogen receptors, or ERs, and a binding affinity similar to estradiol for estrogen receptors (Robertson et al., 1982; Kuiper et al., 1997). Z-4-hydroxy tamoxifen inhibits the growth in culture of normal human epithelial breast cells 100 fold more than Z-tamoxifen (Malet et al., 1988).

Figure 1:
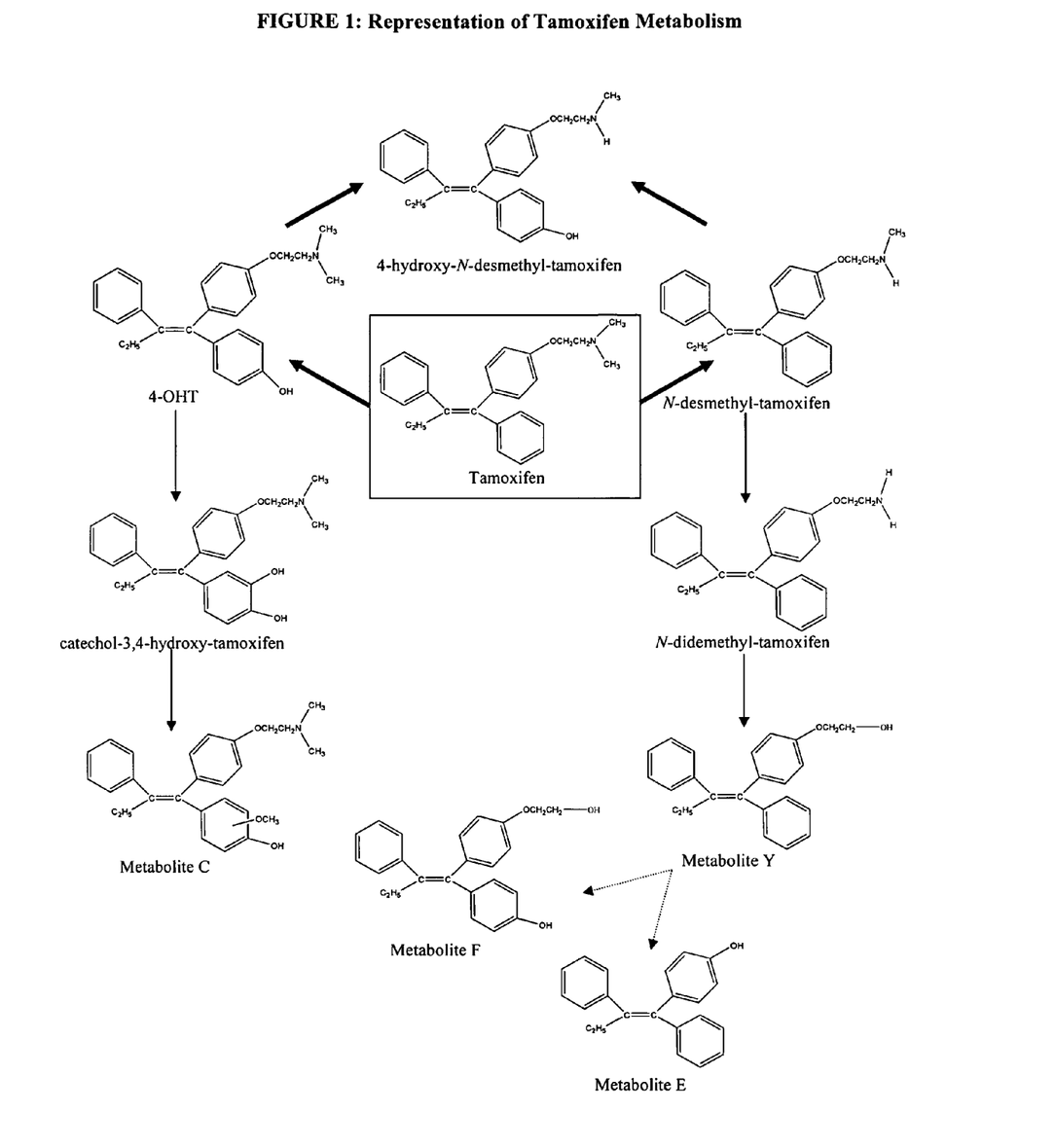
FIG. 1 depicts the metabolism of tamoxifen.

Although 4-hydroxy tamoxifen is a tamoxifen metabolite, its usefulness for benign breast disease is not presaged by previous experience with tamoxifen itself. Tamoxifen is extensively metabolized in humans, as shown in FIG. 1. Thus, its action in vivo is the net result of individual actions by the parent compound and its metabolite compounds competing for the occupation of receptors within target tissues. For example, see Jordan, 1982. Each of these compounds manifests different and unpredictable biological activities in different cells, determined in part by each compound's individual effect on estrogen receptor conformation. That is, estrogen receptor binding of each compound generates a unique receptor-ligand conformation that recruits different cofactors, and results in varying pharmacologies for the different compounds (Wijayaratne et al., 1999; Giambiagi et al., 1988).

Several examples of these varying effects have been documented. For instance, tamoxifen but not 4-hydroxy tamoxifen is a potent rat liver carcinogen. (Carthew et al., 2001; Sauvez et al., 1999). Additionally, tamoxifen but not 4-hydroxy tamoxifen reportedly initiates apoptosis in p53(−) normal human mammary epithelial cells (Dietze et al., 2001). By contrast, 4-hydroxy tamoxifen exhibits a significant inhibitory effect on estrone sulphatase activity in mammary cancer cell lines, while tamoxifen has little or no effect in this regard (Chetrite et al., 1993).

Methods for preparing 4-hydroxy tamoxifen are well known. For example, U.S. Pat. No. 4,919,937 describes a synthesis, derived from Robertson and Katzenellenbogen, 1982, that occurs in stages:

Stage 1—Reaction between 4-(β-dimethylaminoethoxy)-α-ethyldeoxybenzoin and p-(2-tetrahydropyranyloxy) phenylmagnesium bromide;

Stage 2—Separately from stage 1, formation of 1-(4-hydroxyphenyl)-2-phenyl-1-butanone by hydroxylation of 1,2-diphenyl-1-butanone;

Stage 3—Reaction between the products of stages 1 and 2 to form 1-(4-dimethylaminoethoxyphenyl)-1-[p-2-tetrahydropyranyloxy)phenyl]-2-phenylbutan-1-ol;

Stage 4—Dehydration with methanol/hydrochloric acid produces 1-[p-(β-dimethylaminoethoxy)phenyl]-Z-1-(p-hydroxyphenyl)-2-pheny-1-but-1-ene=4-OH-tamoxifen, a mixture of E and Z isomers;

Stage 5—Separation of the E and Z isomers by chromatography and crystallization to constant specific activity.

According to the present invention, 4-hydroxy tamoxifen may be administered to a patient diagnosed with benign breast disease. As used herein, the term "benign breast disease" refers to a constellation of non-malignant aberrations in breast tissue. The aberrations may be proliferative or non-proliferative in nature. Preferably, they will comprise an estrogen-related component, as it is believed that 4-hydroxy tamoxifen primarily exerts its effect by acting on estrogen receptors. Exemplary benign breast diseases treatable by the present methods include adenosis, cysts, duct ectasia, fibroadenoma, fibrosis, hyperplasia, metaplasia and other fibrocystic changes. Each of these diseases, often referred to as "changes" or "conditions" due to their prevalence, have well-defined histological and clinical characteristics.

"Adenosis" refers to generalized glandular disease of the breast. It typically involves an enlargement of breast lobules, which contain more glands than usual. In "sclerosing adenosis," or "fibrosing adenosis," the enlarged lobules are distorted by scar-like fibrous tissue.

"Cysts" are abnormal sacs filled with fluid or semi-solid material, and lined by breast epithelial cells, developing from lobular structures. They begin as excess fluid inside breast glands, but may grow to proportions that stretch surrounding breast tissue, causing pain. "Fibrocysts" are cystic lesions circumscribed by, or situated within, a conspicuous amount of fibrous connective tissue.

"Duct ectasia" refers to a dilation of mammary ducts by lipid and cellular debris. Rupture of the ducts induces infiltration by granulocytes and plasma cells.

"Fibroadenoma" refers to benign tumors that are derived from glandular epithelium and contain a conspicuous stroma of proliferating fibroblasts and connective tissue.

"Fibrosis" simply refers to a prominence of fibrous tissue in the breast.

"Hyperplasia" refers to an overgrowth of cells, where several layers of cells line the basal membrane, without tumor formation. Hyperplasia increases the bulk of mammary tissue. In "epithelial hyperplasia," the cells lining breast ducts and lobules are involved, giving rise to the terms "ductal hyperplasia" and "lobular hyperplasia." Based on a histological determination, hyperplasia may be characterized as "usual" or "atypical."

"Metaplasia" refers to a phenomenon in which a differentiated tissue of one type transforms into a differentiated tissue of another type. Metaplasia often results from an environmental change, and enables cells better to withstand the change.

The present invention also contemplates administration of 4-hydroxy tamoxifen prophylactically. In particular, prophylactic administration is useful in patients at increased risk for developing breast cancer. Many risk factors for breast cancer are well established. For instance, family history of breast cancer, personal history of breast cancer, previous benign breast disease, and previous breast irradiation all place a patient at an elevated risk for developing breast cancer. Particular genetic risk factors include BRCA1, BRCA2, ATM, CHEK-2 and p53 mutations. Certain lifestyle-related risk factors for women include delayed childbirth until after age 30, long-term use of oral contraceptives, and long-term use of hormone replacement therapy. A skilled medical practitioner can evaluate these and other risk factors to determine whether a patient will benefit from prophylactic use of 4-hydroxy tamoxifen. In making such an assessment, a practitioner may employ the Gail model.

4-Hydroxy tamoxifen is particularly useful for preventing benign breast disease in pre-menopausal women. In this population, an anti-estrogen must compete with high amounts of circulating estrogen to occupy estrogen receptors. Because 4-hydroxy tamoxifen has 100-fold more affinity for estrogen receptors than tamoxifen, it is better able to compete for the receptors at low doses. The ability to use a low dose holds particular importance in a prophylactic context, where a patient's exposure to the drug is long-term and side effects are less tolerable.

Pursuant to the present invention, 4-hydroxy tamoxifen may be administered in any dosage form and via any system that delivers the active compound to breast estrogen receptors in vivo. Preferably, the 4-hydroxy tamoxifen is delivered by "percutaneous administration," a phrase that denotes any mode of delivering a drug from the surface of a patient's skin, through the stratum corneum, epidermis, and dermis layers, and into the microcirculation. This is typically accomplished by diffusion down a concentration gradient. The diffusion may occur via intracellular penetration (through the cells), intercellular penetration (between the cells), transappendageal penetration (through the hair follicles, sweat, and sebaceous glands), or any combination of these.

Percutaneous administration of 4-hydroxy tamoxifen offers several advantages. First, it avoids the hepatic metabolism that occurs subsequent to oral administration (Mauvais-Jarvis et al., 1986). Second, percutaneous administration significantly reduces systemic drug exposure, and the attendant risks from non-specifically activating estrogen receptors throughout the body; this, because topical 4-hydroxy tamoxifen is absorbed primarily into local tissues. In particular, when 4-hydroxy tamoxifen is percutaneously applied to breasts, high concentrations accumulate in the breast tissue, presumably due to many estrogen receptors therein, without creating a high plasma concentration (Mauvais-Jarvis et al., supra). Pursuant to the present invention, therefore, 4-hydroxy tamoxifen may be applied to any skin surface, but preferably to one or both breasts.

Although the invention is not constrained to any particular theory, clinically significant side effects of anti-estrogen agents occur when the agents displace estradiol in non-target tissues. Because 4-hydroxy tamoxifen and estradiol have similar binding affinities for estrogen receptors, a competition between them for receptor binding would be approximately equal when the concentration of each compound approximates that of the other. If the 4-hydroxy tamoxifen concentration exceeds the estradiol concentration, the former will be bound preferentially to the estrogen receptors, and vice versa.

Accordingly, doses of 4-hydroxy tamoxifen that result in plasma concentrations less than about 80 pg/mL, or the mean estradiol concentration in normal premenopausal women, are preferred. More preferably, doses of 4-hydroxy tamoxifen will result in plasma concentrations less than about 50 pg/mL. The daily doses to be administered can initially be estimated based upon the absorption coefficients of 4-hydroxy tamoxifen, the breast tissue concentration that is desired, and the plasma concentration that should not be exceeded. Of course, the initial dose may be optimized in each patient, depending on individual responses.

As noted above, by targeting 4-hydroxy tamoxifen to breast tissue, high concentrations can be achieved in that tissue without simultaneously raising 4-hydroxy tamoxifen plasma levels to a point where significant systemic competition for estradiol receptors occurs. At a percutaneous dose of 1 mg/breast/day, 4-hydroxy tamoxifen concentration in breast tissue exceeds normal estradiol concentrations in breast tissue by a factor of 4. (Barrat et al., 1990; Pujol et al., supra). Moreover, 4-hydroxy tamoxifen applied in this manner reaches concentrations in breast tissue that are an order of magnitude higher than concentrations in plasma, i.e., 10:1. By contrast, the breast tissue to plasma ratio of 4-hydroxy tamoxifen following oral administration of tamoxifen is about 5:1.

In a percutaneous formulation, doses on the order of 0.25-2.0 mg/breast/day of 4-hydroxy tamoxifen should achieve the desired result, with doses of about 0.5-1.0 mg/breast/day being preferred. In particular embodiments, the dosage is about 0.25, 0.5, 0.75, 1.0, 1.5 or 2.0 mg/breast/day of 4-hydroxy tamoxifen.

Percutaneous administration can be accomplished mainly in two different ways: (i) by mixing a therapeutically active compound or its non-toxic pharmaceutically acceptable salt with suitable pharmaceutical carriers and, optionally, penetration enhancers to form ointments, emulsions, lotions, solutions, creams, gels or the like, where an amount of said preparation is applied onto a certain area of the skin, or (ii) by incorporating the therapeutically active substance into patches or transdermal delivery systems according to known technology.

The effectiveness of percutaneous drug administration depends on many factors, including drug concentration, surface area of application, time and duration of application, previous irradiation, skin hydration, skin temperature, physicochemical properties of the drug, and partitioning of the drug between the formulation and the skin. Drug formulations intended for percutaneous use take advantage of these factors to achieve optimal delivery. Such formulations often comprise penetration enhancers that improve percutaneous absorption by reducing the resistance of the stratum corneum by reversibly altering its physiochemical properties, changing hydration in the stratum corneum, acting as co-solvent, or changing the organization of lipids and proteins in the intercellular spaces. Such enhancers of percutaneous absorption include surfactants, DMSO, alcohol, acetone, propyleneglycol, polyethylene glycol, fatty acids or fatty alcohols and their derivatives, hydroxyacids, pyrrolidones, urea, essential oils, and mixtures thereof. In addition to chemical enhancers, physical methods can increase percutaneous absorption. For example, occlusive bandages induce hydration of the skin. Other physical methods include iontophoresis and sonophoresis, which use electrical fields and high-frequency ultrasound, respectively, to enhance absorption of drugs that are poorly absorbed due to their size and ionic characteristics.

The many factors and methods relating to percutaneous drug delivery are reviewed in REMINGTON: THE SCIENCE AND PRACTICE OF PHARMACY, Alfonso R. Gennaro (Lippincott Williams & Wilkins, 2000), at pages 836-58, and in PERCUTANEOUS ABSORPTION: DRUGS COSMETICS MECHANISMS METHODOLOGY, Bronaugh and Maibach (Marcel Dekker, 1999). As these publications evidence, those in the pharmaceutical field can manipulate the various factors and methods to achieve efficacious percutaneous delivery.

4-Hydroxy tamoxifen is a large and very lipophilic molecule; hence, without assistance from penetration enhancers it poorly penetrates the skin. Accordingly, formulations of 4-hydroxy tamoxifen used in the present invention preferably comprise one or more penetration enhancers. Alcohols are preferred enhancers because 4-hydroxy tamoxifen is soluble in alcohol. Isopropyl myristate also is a preferred enhancer.

For percutaneous administration, 4-hydroxy tamoxifen may be delivered in an ointment, cream, gel, emulsion (lotion), powder, oil or similar formulation. To this end, the formulation may comprise customary excipient additives, including vegetable oils such as almond oil, olive oil, peach kernel oil, groundnut oil, castor oil and the like, animal oils, DMSO, fat and fat-like substances, lanolin lipoids, phosphatides, hydrocarbons such as paraffins, petroleum jelly, waxes, detergent emulsifying agents, lecithin, alcohols, carotin, polyols or polyglycols such as glycerol (or glycerine), glycerol ethers, glycols, glycol ethers, polyethylene glycol, polypropylene glycol, non-volatile fatty alcohols, acids, esters, volatile alcoholic compounds, urea, talc, cellulose derivatives, coloring agents, antioxidants and preservatives.

According to the present invention, 4-hydroxy tamoxifen also may be delivered via a transdermal patch. In one embodiment, the patch comprises a reservoir for the 4-hydroxy tamoxifen formula. The patch may comprise (a) a solution-impermeable backing foil, (b) a layer-like element having a cavity, (c) a microporous or semi-permeable membrane, (d) a self-adhesive layer, and (e) optionally, a removable backing film. The layer-like element having a cavity may be formed by the backing foil and the membrane. Alternatively, the patch may comprise (a) a solution-impermeable backing foil, (b) an open-pored foam, a closed-pore foam, a tissue-like layer or a fibrous web-like layer as reservoir, (c) if the layer according to (b) is not self-adhesive, a self-adhesive layer, and (d) optionally a removable backing film.

In preferred embodiments of the invention, 4-hydroxy tamoxifen is formulated in a hydroalcoholic gel. The amount of 4-hydroxy tamoxifen in such a gel may range from about 0.001 to about 1.0 gram of 4-hydroxy tamoxifen per 100 grams of gel. Preferably, it ranges from about 0.01 to about 0.20 grams of 4-hydroxy tamoxifen per 100 grams of gel. Thus, the amount of 4-hydroxy tamoxifen may be about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19 or 0.20 grams per 100 grams of gel.

It is also preferred that 4-hydroxy tamoxifen formulations comprise one or more fatty acid esters as a penetration enhancer. One highly preferred example of a fatty acid ester penetration enhancer is isopropyl myristate. When isopropyl myristate is used in a gel, the amount may range from about 0.1 to about 5.0 grams per 100 grams of gel. Preferably, the amount of isopropyl myristate ranges from about 0.5 to about 2.0 grams per 100 grams of gel. Thus, the amount of isopropyl myristate may be about 0.5, 0.6, 0.7, 0.8, 0.9, 1.0, 1.1, 1.2, 1.3, 1.4, 1.5, 1.6, 1.7, 1.8, 1.9, or 2.0 grams per 100 grams of gel.

4-Hydroxy tamoxifen formulations of the invention generally will comprise one or more nonaqueous vehicles, such as alcoholic vehicles. These vehicles should be capable of dissolving both 4-hydroxy tamoxifen and any penetration enhancer used. They also should have a low boiling point, preferably less than 100° C. at atmospheric pressure, to permit rapid evaporation upon contact with the skin. Examples of suitable non-aqueous vehicles include ethanol, isopropanol and ethyl acetate. Ethanol and isopropanol are preferred. In particular, ethanol effectively contributes to the percutaneous absorption of 4-hydroxy tamoxifen by rapidly evaporating upon contact with skin. The amount of absolute nonaqueous vehicle in a gel formulation generally ranges between 35% and 99.9% by weight, preferably between 50% and 85%, more preferably between 60% and 75%. Thus, the amount of absolute nonaqueous vehicle in a gel formulation may be about 60%, 61%, 62%, 63%, 64%, 65%, 66%, 67%, 68%, 69%, 70%, 71%, 72%, 73%, 74% or 75%.

Formulations also may comprise an aqueous vehicle, which permits solubilization of any hydrophilic molecules in a formulation, and also promotes moisturization of the skin. An aqueous vehicle also can regulate pH. Aqueous vehicles include alkalinizing and basic buffer solutions, including phosphate buffered solutions (e.g., dibasic or monobasic sodium phosphate), citrate buffered solutions (e.g., sodium citrate or potassium citrate) and simply purified water. The amount of an aqueous vehicle preferably ranges between 0.1% and 65% by weight of the pharmaceutical composition, more preferably between 15% and 50%, and still more preferably between 25% and 40%. Thus, the amount of an aqueous vehicle may be about 25%, 26%, 27%, 28%, 29%, 30%, 31%, 32%, 33%, 340%, 35%, 36%, 37%, 38%, 39% or 40%. In the case that formulations contain an aqueous vehicle, the amount of absolute alcoholic vehicle in a formulation is preferably from about 60% to about 75%

Additionally, 4-hydroxy tamoxifen formulations may comprise one or more gelling agents to increase the viscosity of a formulation and/or to function as a solubilizing agent. Depending on the gelling agent's nature, it may constitute between 0.1% and 20% by weight of a formulation, preferably between 0.5% and 10%, and still more preferably between 0.5% and 5%. Thus, the amount of a gelling agent may be about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10%. Preferred gelling agents include carbomers, cellulose derivatives, poloxamers and poloxamines. More particularly, preferred gelling agents are chitosan, dextran, pectins, natural gum and cellulose derivatives such as ethyl cellulose, hydroxypropyl cellulose, hydroxyethyl cellulose, hydroxypropyl methyl cellulose (HPMC), carboxymethyl cellulose (CMC), and the like. One highly preferred gelling agent is hydroxypropyl cellulose.

When a formulation comprises a gelling agent, in particular a non-preneutralized acrylic polymer, it may advantageously also comprise a neutralizing agent. The neutralizing agent/gelling agent ratio preferably is between 10:1 and 0.1:1, more preferably between 7:1 and 0.5:1, and still more preferably between 4:1 and 1:1. Thus, the neutralizing agent/gelling agent ratio may be about 7:1, 6:1, 5:1, 4:1, 3:1, 2:1, 1:1 or 0.5:1. A neutralizing agent should form, in the presence of the polymer, salts that are soluble in the vehicle. A neutralizing agent also should permit optimum swelling of polymer chains during neutralization of charges and formation of polymer salts. Useful neutralizing agents include sodium hydroxide, ammonium hydroxide, potassium hydroxide, arginine, aminomethylpropanol, trolamine and tromethamine. Those skilled in the art will select a neutralizing agent according to the type of gelling agent employed in a formulation. When cellulose derivatives are used as gelling agents, however, no neutralizing agents are required.

Table 1 describes the composition of two highly preferred 4-hydroxy tamoxifen gel formulations.

TABLE 1

Composition of 4-Hydroxy Tamoxifen Gel Formulations

| Ingredient | Quantity per 100 g of gel | |
|---|---|---|
| | 20 mg 4-OHT Gel | 57 mg 4-OHT Gel |
| 4-Hydroxy Tamoxifen | 0.02 g | 0.057 g |
| Absolute Ethyl Alcohol, EP USP | 66.5 g | 66.5 g |
| Isopropyl myristate, EP USP | 1 g | 1 g |

TABLE 1-continued

Composition of 4-Hydroxy Tamoxifen Gel Formulations

| Ingredient | Quantity per 100 g of gel | |
|---|---|---|
| | 20 mg 4-OHT Gel | 57 mg 4-OHT Gel |
| Hydroxypropylcellulose, EP USP | 1.5 g | 1.5 g |
| Phosphate Buffer (pH 7, diluted 1:4) | q.s. 100 g | q.s. 100 g |

Reference to the following, illustrative examples will help to provide a more complete understanding of the invention.

EXAMPLE 1

Demonstration of Percutaneous 4-Hydroxy Tamoxifen Delivery

Four patients with breast cancer received [$^3$H]-4-hydroxy tamoxifen in an alcoholic solution applied directly to the breasts at specified intervals between 12 hours to 7 days prior to surgery to excise diseased tissue. After surgery, both the excised tissue and the normal breast tissue surrounding the tumor contained radioactivity (Kuttenn et al., 1985).

In a follow-up study, 9 of 12 patients scheduled for surgical excision of hormone-dependent breast cancer received Z-[$^3$H]-4-hydroxy tamoxifen (80 µCi) in a 60% alcoholic solution, and 3 patients received Z-[$^3$H]-tamoxifen (80 µCi) for comparison. The patients received [$^3$H]-labeled drug applied directly on the affected breasts at specified intervals ranging from 12 hours to 7 days before surgery to excise diseased tissue. Breast tissue from three regions: the tumor, tissue immediately surrounding the tumor, and normal tissue, was excised and immediately frozen in liquid nitrogen. Additionally, plasma and urine samples were obtained at scheduled intervals and frozen until analysis.

Table 2 shows results from the analyses performed. 4-Hydroxy tamoxifen concentrated predominantly in the cytosolic and nuclear fractions of breast tissue, where estrogen receptors are present. In these intracellular sites, 4-hydroxy tamoxifen remained unmetabolized except for limited isomerization from the Z to the E form. Retention in the breast lasted approximately 4 days in the 4-hydroxy tamoxifen group, but was shorter and far weaker in the tamoxifen group.

TABLE 2

[$^3$H]-4-Hydroxy Tamoxifen and Metabolites Identified in Breast Tumor Tissue Following Percutaneous Administration of Z-[$^3$H]-4-Hydroxy Tamoxifen to the Affected Breast

| Metabolites | % Metabolites in Breast Tissue | | | | |
|---|---|---|---|---|---|
| | 12 hr[1] | 24 hr | 36 hr | Day 4 | Day 7 |
| 4-Hydroxy Tamoxifen | 97 | 94 | 78 | 70 | 65 |
| N-Desmethyl-4-Hydroxy Tamoxifen | 2 | 4 | 14 | 20 | 16 |
| Bisphenol | 1 | 2 | 3 | 8 | 8 |
| N-Desmethyl tamoxifen | | | <1 | <1 | 3-4 |
| Tamoxifen | | | | <1 | 2 |

[1]Time after administration of Z-[$^3$H]-4-hydroxy tamoxifen

The percentage of radioactivity identified as [$^3$H]-4-hydroxy tamoxifen in breast tissue after percutaneous administration decreased slowly over seven days (from 97% to 65%). During this period a progressive isomerization of the Z isomer into the E isomer occurred, with similar percentages observed at day 7 (32% and 33%).

The radioactivity in blood due to [$^3$H]-4-hydroxy tamoxifen increased gradually, with a plateau from days 4 to 6. This contrasts with [$^3$H]-tamoxifen, which rapidly appeared in the blood, plateauing at 2 days. At 36 hours following percutaneous [$^3$H]-4-hydroxy tamoxifen administration, only 0.5% of the radioactivity administered showed in the blood.

In contrast to the near absence of 4-hydroxy tamoxifen metabolism in the breast tissue, marked metabolism occurred in blood. In blood, at 24 hours after administration, 68% of radioactivity represented 4-hydroxy tamoxifen, 18% represented N-desmethyl-4-hydroxy tamoxifen, and 11% represented bisphenol.

Peak urinary elimination occurred at a later time following percutaneous administration of 4-hydroxy tamoxifen compared to percutaneous tamoxifen. Following application of 4-hydroxy tamoxifen, a progressive increase of metabolites, mostly N-desmethyl-4-hydroxy tamoxifen and bisphenol, was observed in the urine.

This example demonstrates that percutaneous application of 4-hydroxy tamoxifen to the breasts results in a substantial and lasting local tissue concentration of the drug, with minimal metabolism, stable and very low plasma concentrations, and slow elimination via the urine.

EXAMPLE 2

Demonstration of the Pharmacokinetics and Pharmacodynamics of Percutaneously Administered 4-OH-Tamoxifen Compared to 20 mg of Oral Tamoxifen This study compared the tissue and plasma concentrations of 4-hydroxy tamoxifen after percutaneous administration via a hydroalcoholic gel with tissue and plasma concentrations of 4-hydroxy tamoxifen after oral administration of tamoxifen (Pujol, 1995).

Thirty-one patients scheduled for breast cancer surgery were randomly assigned to 1 of 5 groups. They received treatment with either oral tamoxifen or percutaneous 4-hydroxy tamoxifen as outlined in Table 3. Treatment was daily and lasted for 3-4 weeks prior to surgery. The study evaluated three different doses of 4-hydroxy tamoxifen (0.5, 1, or 2 mg/day) and two areas of application (either to both breasts or to a large surface of skin including arms, forearms, and shoulders). One group of patients received 20 mg/day (10 mg b.i.d.) of oral tamoxifen (Nolvaldex®).

TABLE 3

Treatment Groups

| Group | N | Drug | Application Site | Dose mg/breast/day | Total Daily Dose (mg/day) |
|---|---|---|---|---|---|
| 1 | 6 | PO tamoxifen | — | — | 20[a] |
| 2 | 6 | 4-OHT gel | both breasts | 0.25 | 0.5 |
| 3 | 5 | 4-OHT gel | both breasts | 0.50 | 1 |
| 4 | 5 | 4-OHT gel | arms, forearms, and shoulders | — | 1 |
| 5 | 6 | 4-OHT gel | arms, forearms, and shoulders | — | 2[b] |

[a]10 mg b.i.d.
[b]divided into 2 daily applications; 1 mg in the morning and 1 mg in the evening The 4-hydroxy tamoxifen gel (20 mg of 4-hydroxy tamoxifen/100 g of hydroalcholic gel; Besins-International Laboratories) was packaged in a pressurized dose-metering pump that delivered 1.25 g of gel/metered dose (i.e., 0.25 mg of 4-hydroxy tamoxifen/dose).

During surgery, two samples (1 cm$^3$ each) of breast tissue were excised, one tumoral and the other macroscopically normal. They were immediately frozen in liquid nitrogen until assayed. Blood samples were obtained on the day of and the day prior to surgery. All tissue and plasma samples were analyzed for 4-hydroxy tamoxifen concentration by gas chromatograph/mass spectrometry (GC-MS).

Pre and post-treatment blood samples were assayed for complete blood counts (CBC), bilirubin, serum glutamic-pyruvic transaminase (SGPT), serum glutamic-oxaloacetic transaminase (SGOT), alkaline phosphatase, creatinine, estradiol, follicle-stimulating hormone (FSH), luteinizing hormone (LH), sex hormone-binding globulin (SHBG), cholesterol, high-density lipoprotein (HDL), low-density lipoprotein (LDL), triglycerides, fibrinogen, and anti-thrombin III.

Table 4 below summarizes the concentration of 4-hydroxy tamoxifen found in breast tissue and plasma. Normal and tumor breast tissues contained similar concentrations of 4-hydroxy tamoxifen in all five treatment groups. 4-hydroxy tamoxifen concentrated at higher amounts in breast tissue when the gel was applied directly to the breasts, rather than to other large skin surfaces.

the oral tamoxifen group, consistent with the biologic effects of this drug observed in other studies.

EXAMPLE 3

Demonstration of Tolerance and Pharmacokinetics of Percutaneously Administered 4-OH-Tamoxifen in Healthy Women This study demonstrates the tolerance and pharmacokinetics of topically applied 4-hydroxy tamoxifen gel in healthy premenopausal women, aged 18-45. Each participant applied the gel daily for the duration of two menstrual cycles.

Three doses and two gel concentrations were tested, as summarized in Table 5. For Groups A-C, the gel, containing 20 mg of 4-hydroxy tamoxifen/100 g, was dispensed from a pressurized dose-metering pump that delivered 0.25 mg of 4-hydroxy tamoxifen/dose. The study of Group C was suspended because the quantity of gel was too large to be applied to a single breast. Groups D and E received a more concentrated gel that contained almost 3 times as much 4-hydroxy tamoxifen: 57 mg of 4-hydroxy tamoxifen/100 g, or 50 mg of 4-hydroxy tamoxifen/100 mL of gel. This more concentrated gel also was delivered by a dose-metering pump that supplied 0.25 mg of 4-hydroxy tamoxifen/dose.

TABLE 4

Concentrations of 4-hydroxy tamoxifen

| | | Mean ± SD 4-hydroxy tamoxifen (Range) | | | |
|---|---|---|---|---|---|
| | | Plasma Concentrations (pg/mL) | | Normal Tissue | Tumor |
| Group | N | Day Pre-Surgery | Day of Surgery | (pg/g) | (pg/g) |
| 1 | 6 | 2326 ± 585 (1371-2959)$^a$ | 2317 ± 1098 (881-4176) | 10215 ± 2151 (5873-11511) | 12453 ± 3751 (9568-18904)$^a$ |
| 2 | 6 | 0 (0-0)$^a$ | 17 ± 27 (0$^c$-61) | 353 ± 513 (0$^d$-1317) | 1447 ± 2673 (0$^f$-6889) |
| 3 | 5 | 164 ± 131 (29-279)$^b$ | 62 ± 71 (28-190) | 1112 ± 1125 (197-2979 | 1877 ± 2472 (345-6211) |
| 4 | 5 | 94 ± 76 (35-201)$^b$ | 13 ± 29 (0$^c$-65) | 140 ± 130 (0$^e$-270) | 552 ± 357 (271-1150) |
| 5 | 6 | 78 ± 138 (0$^e$-284)$^b$ | 73 ± 114 (0$^c$-244) | 992 ± 2195 (0$^d$-5462) | 224 ± 312 (0$^d$-799) |

$^a$n = 5
$^b$n = 4
$^c$4 patients had undetectable levels of 4-hydroxy tamoxifen (LOQ = 20 pg/ml)
$^d$3 patients had undetectable levels of 4-hydroxy tamoxifen
$^e$2 patients had undetectable levels of 4-hydroxy tamoxifen
$^f$1 patient had undetectable levels of 4-hydroxy tamoxifen Side effects did not pose a significant problem. Cutaneous treatment did not cause any local irritation. One woman in Group 2 (0.5 mg/day of 4-hydroxy tamoxifen gel) reported dizzy spells, cystitis, and mild vaginitis occurring on the seventh day of treatment. One woman in Group 1 (oral tamoxifen) reported hot flashes and mild vaginitis on the fifth day of treatment.

No differences existed between the pre- and post treatment blood samples for any of the hematology or serum chemistry evaluations in the patients who received 4-hydroxy tamoxifen gel. However, a statistically significant decrease in anti-thrombin III and fibrinogen and a statistically significant increase in platelet and lymphocyte counts were observed in

TABLE 5

Treatment Groups

| Group | N | Dose (mg/day) | Gel Concentration (mg of 4-OHT/g of gel) | Treatment |
|---|---|---|---|---|
| A | 12 | 0.5 | 20 mg/100 g | 1 metered dose/breast/day |
| B | 8 | 1 | 20 mg/100 g | 2 metered doses/breast/day |
| C | 2 | 2 | 20 mg/100 g | study was interrupted |
| D | 12 | 1 | 57 mg/100 g | 2 metered doses/breast/day |
| E | 12 | 2 | 57 mg/100 g | 4 metered doses/breast/day |

At the end of a menstrual cycle, each patient received a single dose, after which serial blood samples were collected at 0, 0.5, 1, 1.5, 2, 3, 4, 6, 12, 18, 24, 36, 48, and 72 hours.

On the first day of the following menstruation, treatment, which consisted of daily application of the gel over two menstrual cycles, began. Blood samples were collected 24 hours following the morning application of gel on days 7, 20 and 25 of the first and second cycles. On the last day of administration, day 25 of the second menstrual cycle, serial blood samples were collected prior to application and at 0.5, 1, 1.5, 2, 3, 4, 6, 12, 18, 24, 36, 48, and 72 hours after application of the gel. The samples were analyzed for 4-hydroxy tamoxifen, estradiol, progesterone, FSH and LH.

Plasma concentrations of 4-hydroxy tamoxifen remained detectable 72 hours after the last gel application. Therefore, to ensure that data points were obtained until 4-hydroxy tamoxifen became undetectable in the blood, additional blood samples were collected from some participants at intervals up to 92 days following the last application of gel.

Table 6 displays the mean±standard deviation (SD) plasma concentrations of 4-hydroxy tamoxifen, with ranges in parentheses. A single 0.5 mg dose did not produce detectable plasma concentrations of 4-hydroxy tamoxifen, but 6 of 12 patients had detectable plasma concentrations (>5 pg/mL) after a single dose of 1 mg.

TABLE 6

Mean ± SD Plasma Concentrations of 4-hydroxy tamoxifen in Healthy Women Following Daily Cutaneous Administration for Two Menstrual Cycles

| Cycle | Day | Time after Application (hr) | 0.5 mg/day (n = 12)[1] | 1 mg/day (n = 8)[1] | 1 mg/day (n = 12)[2] | 2 mg/day (n = 12)[2] |
|---|---|---|---|---|---|---|
| First | 1 | 0 | (0-17.2) | (0-13.9) | (0-9.5) | (0-0) |
|  | 7 | 24 | 6.4 ± 5.6 (<LOQ-16.8) | 15.2 ± 9.7 (<LOQ-26.8) | 14.4 ± 13.1 (<LOQ-37.9) | 26.9 ± 18.2 (8.9-71.3) |
|  | 20 | 24 | 13.6 ± 7.9 (<LOQ-25.9) | 17.3 ± 9.5 (<LOQ-29.8) | 18.1 ± 15.8 (<LOQ-44.5) | 44.0 ± 29.2 (10.5-117.5) |
|  | 25 | 24 | 23.9 ± 23.4 (<LOQ-73.1) | 15.5 ± 6.6 (6.4-25.0) | 19.8 ± 16.2 (6.2-57.0) | 45.4 ± 31.0 (17.9-120.1) |
| Second | 7 | 24 | 25.2 ± 16.1 (6.5-61.7) | 17.4 ± 11.2 (5.7-39.6) | 22.2 ± 16.4 (9.0-64.4) | 42.2 ± 24.8 (18.2-98.0) |
|  | 20 | 24 | 15.7 ± 14.0 (<LOQ-52.3) | 14.8 ± 6.5 (5.4-24.8) | 24.4 ± 20.1 (<LOQ-65.4) | 38.9 ± 27.1 (18.7-119.7) |
|  | 25 | 0[3] | 10.8 ± 9.9 (<LOQ-36.4) | 15.7 ± 17.1 (<LOQ-56.4) | 27.2 ± 20.8 (8.0-72.1) | 43.2 ± 27.7 (16.9-120.3) |
|  |  | 0.5 | 10.9 ± 7.4 (<LOQ-26.0) | 13.5 ± 9.1 (<LOQ-27.7) | 25.9 ± 18.7 (8.7-69.2) | 44.5 ± 29.9 (13.6-124.5) |
|  |  | 1 | 10.4 ± 7.8 (<LOQ-26.7) | 10.8 ± 6.6 (<LOQ-23.8) | 28.7 ± 19.5 (8.8-69.2) | 40.5 ± 25.1 (14.2-106.7) |
|  |  | 1.5 | 9.0 ± 8.2 (<LOQ-25.1) | 11.8 ± 8.0 (<LOQ-23.6) | 25.6 ± 17.8 (7.5-67.0) | 36.8 ± 21.1 (15.9-90.0) |
|  |  | 2 | 11.8 ± 9.5 (<LOQ-26.9) | 10.7 ± 6.9 (<LOQ-24.7) | 25.1 ± 18.0 (6.9-67.3) | 36.8 ± 21.6 (13.0-83.7) |
|  |  | 3 | 10.0 ± 7.9 (<LOQ-23.1) | 11.4 ± 7.9 (<LOQ-28.1) | 24.8 ± 20.5 (9.0-69.9) | 36.1 ± 20.6 (11.9-89.4) |
|  |  | 4 | 9.2 ± 8.3 (<LOQ-25.3) | 11.2 ± 7.3 (<LOQ-25.7) | 26.8 ± 23.3 (6.4-78.1) | 38.1 ± 21.2 (16.5-92.0) |
|  |  | 6 | 11.4 ± 8.5 (<LOQ-26.6) | 10.7 ± 6.4 (<LOQ-22.8) | 25.0 ± 18.2 (9.0-65.3) | 41.0 ± 29.1 (14.0-123.8) |
|  |  | 12 | 11.0 ± 9.7 (<LOQ-29.1) | 11.8 ± 7.8 (<LOQ-28.1) | 28.3 ± 22.9 (6.4-74.6) | 45.1 ± 30.6 (18.7-126.8) |
|  |  | 18 | 9.7 ± 8.8 (<LOQ-24.9) | 12.2 ± 8.3 (<LOQ-29.6) | 23.4 ± 17.4 (8.1-57.9) | 39.8 ± 25.5 (16.0-107.3) |
|  | 26 | 24 | 12.4 ± 9.4 (<LOQ-34.4) | 18.6 ± 14.2 (<LOQ-40.1) | 26.0 ± 19.6 (8.9-61.9) | 44.0 ± 33.0 (15.8-132.5) |
|  |  | 36 | 10.9 ± 6.9 (5.0-25.8) | 13.4 ± 7.5 (<LOQ-25.4) | 25.7 ± 18.4 (8.8-61.3) | 42.1 ± 31.5 (15.1-129.3) |
|  | 27 | 48 | 12.1 ± 6.5 (4.8-26.6) | 12.5 ± 6.0 (<LOQ-19.6) | 22.0 ± 16.0 (5.6-50.2) | 38.1 ± 25.3 (17.5-110.0) |
|  | 28 | 72 | 9.9 ± 7.1 (<LOQ-22.3) | 9.9 ± 5.8 (<LOQ-19.6) | 18.9 ± 12.4 (5.6-37.8) | 33.2 ± 22.2 (17.7-98.0) |
|  |  | +5 days | — | 5.8 ± 5.2 (<LOQ-12.4) | 11.4 ± 8.2 (<LOQ-25.8) | 20.4 ± 17.3 (9.1-71.6) |
|  |  | +8 days | <LOQ | (<LOQ-17.4) | (0-14.8) | 10.8 ± 13.4 (<LOQ-52.0) |
|  |  | +12 days | (maximum 9.09) | (<LOQ-7.0) | (0-<LOQ) | (0-30.4) |
|  |  | +20 days | 0 | <LOQ | (0-<LOQ) | (0-<LOQ) |

[1]Gel concentration was 20 mg of 4-hydroxy tamoxifen per 100 g of gel.
[2]Gel concentration was 57 mg of 4-hydroxy tamoxifen per 100 g of gel.
[3]Timepoint 0 is 24 hours after the application on Day 24 and prior to the final application on Day 25.
LOQ = limit of quantification (<5 pg/mL)

Figure 2:
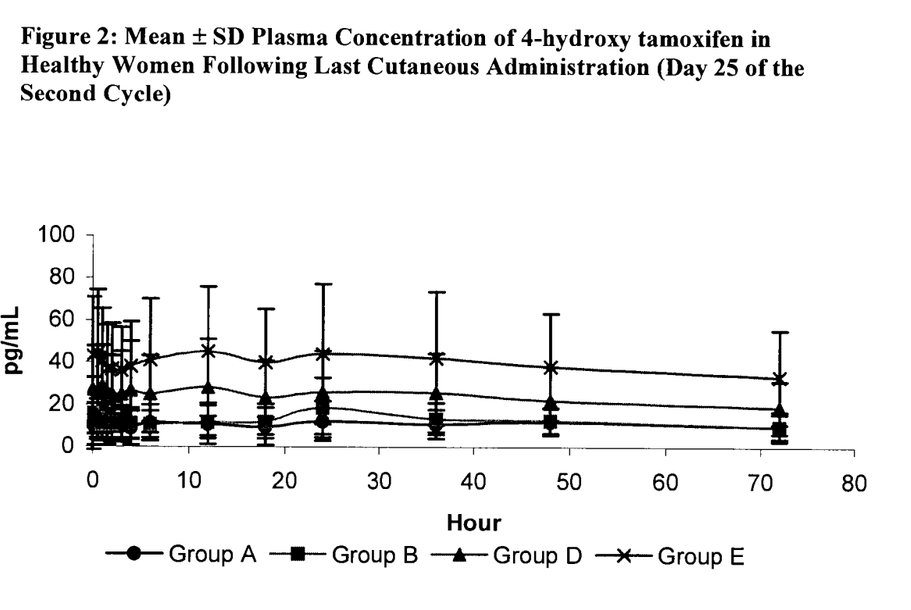
FIG. 2 depicts plasma concentrations of 4-hydroxy tamoxifen in healthy women following cutaneous administration.

FIG. 2 shows a plasma concentration-time curve, following the last administration on day 25 of the second menstrual cycle. Table 7 shows mean pharmacokinetic parameters that relate to the last administration, on day 25 of the second menstrual cycle.

TABLE 7

Mean Pharmacokinetic Parameters of 4-hydroxy tamoxifen in Healthy Women Following the Last Administration

| Parameter | Mean ± SD (Range is indicated in parenthesis) | | | |
| --- | --- | --- | --- | --- |
| | 0.5 mg/day (n = 12)[a] | 1 mg/day (n = 8)[a] | 1 mg/day (n = 12)[b] | 2 mg/day (n = 12)[b] |
| $C_{max}$ (pg/mL) | 17.0 ± 8.5 (7.6-34.4) | 21.0 ± 4.0 (<LOQ-40.1) | 35.1 ± 22.4 (9.9-78.1) | 51.6 ± 31.7 (22.1-132.5') |
| $t_{max}$ (hr) | 40 ± 81 (0.5-288) | 24 ± 18 (0.5-48) | 12.8 ± 14.9 (1-36) | 11.8 ± 12.3 (0.5-36) |
| $t_{1/2}$ (hr) | — | — | (58-118) | (49-101) |
| $AUC_{0-24}$ (pg · hr/mL) | 256.3 ± 205.3 (24.6-651.1) | 300.9 ± 190.8 (0-693.6) | 619 ± 466 (187-1522) | 998 ± 653 (424-2778) |
| $C_{av} = AUC_{0-24}/24$ (pg/mL) | 10.7 ± 8.5 (1.0-27.1) | 12.5 ± 7.9 (0-28.9) | 25.8 ± 19.4 (7.8-63.4) | 41.6 ± 27.2 (17.7-115.8) |
| T(1stC < LOQ) (hr) | — | 274 ± 141 (144-480) | 236 ± 72 (144-384) | 326 ± 97 (192-480) |

[a]Gel concentration was 20 mg of 4-hydroxy tamoxifen per 100 g of gel.
[b]Gel concentration was 57 mg of 4-hydroxy tamoxifen per 100 g of gel.
$AUC_{0-24}$ = area under the concentration-time curve for 0-24 hours; $C_{av}$ = Calculation of area under the curve over 24 hours ($AUC_{0-24}$) divided by 24 hours; $C_{max}$ = maximal concentration in plasma; $t_{1/2}$ = half-life; T(1stC < LOQ) = first timepoint at which the plasma concentration was below the limit of quantification; $t_{max}$ = time of maximal concentration in plasma.

The data are consistent with a dose response across the three doses tested (0.5, 1, and 2 mg). The more concentrated gel was better absorbed, by approximately double, than the less concentrated gel, based on AUC and $C_{av}$.

Biological tolerance was excellent in all 36 patients. The treatment did not affect FSH, LH, estradiol, or progesterone hormone levels during the menstrual cycles. Moreover, echographic examination of the ovaries at the end of treatment was normal in all patients, showing normal sized developing follicles. One patient developed an allergic reaction to the gel, and 10 reported facial acne (5 of which had a past history of acne).

In summary, this study indicates that the exposure to 4-hydroxy tamoxifen after topical application increases with dose, that plasma concentrations of 4-hydroxy tamoxifen are lower than typical estradiol concentrations (80 pg/mL), and that there is no detectable laboratory or clinical evidence of systemic effects.

CITED PUBLICATIONS

Barrat, J., B. de LignilIIres, L. Marpeau, L. Larue, S. Fournier, K. Nahoul, G. Linares, H. Giorgi, and G. Contesso, Effet in vivo de l'administration locale de progestIIrone sur l'activitII mitotique des galactophores humains, J. Gynecol. Obstet. Biol. Reprod. 19:269-274 (1990) (French).

Bodian, C. A., K. H. Perzin, R. Lattes, P. Hoffman and Abernathy, Prognostic significance of benign proliferative breast disease, Cancer, 71(12): 3896-907 (1993).

Bronaugh and Maibach, Percutaneous Absorption: Drugs Cosmetics Mechanisms Methodology, Marcel Dekker 1999.

Carter, C. L., D. K. Corle, M. S. Micozzi, A. Schatzkin and P. R. Taylor, A prospective study of the development of breast cancer in 16,692 women with benign breast disease, Am. J. Epidemiol., 128: 467-77 (1988).

Carthew, P., P. N. Lee, R. E Edwards, R. T. Heydon, B. M. Nolan, E. A. Martin, Cumulative exposure to tamoxifen: DNA adducts and liver cancer in the rat, Arch. Toxicol., 75: 375-80 (2001).

Chemite, G., C. Varin, L. Delalonde, J. R. Pasqualini, Effect of promegestone, tamoxifen, 4-hydroxytamoxifen and ICT 164,384 on the oestrone sulphatase activity of human breast cancer cells, Anticancer Res., 13(4) 931-4 (July-August 1993).

Dietze, E. C., L. E. Caldwell, S. L. Grupin, M. Mancini, and V. L. Seewald, Tamoxifen, but not 4-hydroxytamoxifen initiates apoptosis in p53(−) normal human mammary epithelial cells by inducing mitochondrial depolarization, J. Biol. Chem., 276(7): 5384-94 (Feb. 16, 2001).

Dupont, W. D. and D. L. Page, Risk factors for breast cancer in women with proliferative breast disease, New England J. Med., 312(3): 146-51 (1985).

Dupont, W. D., D. L. Page, F. F. Parl, C. L. Vnencak-Jones, W. D. Plummer, M. S. Rados and P. A. Schuyler, Long-term risk of breast cancer in women with fibroadenoma, New England J. Med, 3310(1): 10-15 (1994).

Fentiman, I. S., Tamoxifen and mastalgia. An emerging indication, Drugs 32: 477-80 (1986).

Fentiman, I. S., M. Caleffi, H. Hamed, and M. A. Chaudary, Dosage and duration of tamoxifen treatment for mastalgia: a controlled trial, British Journal of Surgery 75: 845-46 (1988).

Fentiman, I. S., M. Caleffi, H. Hamed, and M. A. Chaudary, Studies of tamoxifen in women with mastalgia, British Journal of Clinical Practice, Supplement 68, 43(11): 34-36 (1989))

Fitzgibbons, P. L.; D. E. Henson, and R. V. Hutter, Benign breast changes and the risk for subsequent breast cancer: an update of the 1985 consensus statement. Cancer Committee of the college of American Pathologists, Arch. Pathol. Lab. Med., 122: 1053-55 (1998)

Giambiagi, N. and J. R. Pasqualini, Immunological differences between the estradiol-, tamoxifen and 4-hydroxytamoxifen estrogen receptor complexes detected by two monoclonal antibodies, J. Steroid Biochem., 30(1-6): 213-7 (1988).

Hoxumi, Y., M. Kawano, T. Saito and M. Miyata, Effect of tamoxifen on serum lipid metabolism, J. Clin. Endocrinol. Metab., 83(5): 1633-35 (1998).

Jordan, V. C., Metabolites of tamoxifen in animals and man: identification, pharmacology, and significance, Breast Cancer Res. Treat., 2(2) 123-38 (1982).

Korenman S G, Stevens R H, Carpenter L A, Robb M, Niswender G D, Sherman B M. Estradiol radioimmunoassay without chromatography: procedure, validation and normal values, J. Clin. Endocrinol Metab., 38:718-20 (1974).

Krieger, N. and R. A. Hiatt, Risk of breast cancer after benign breast diseases. Variation by histologic type, degree of atypia, age at biopsy and length of follow-up, Am. J. Epidemiol., 135: 619-31 (1992).

Kuiper, G. G. J. M., B. Carlsson, K. Grandien, E. Enmark, J. Heggblad, S, Nilsson, J. Gustafsson, Comparison of the ligand binding specificity and transcript tissue distribution of estrogen receptors α and β, Endocrinology, 138:863-870 (1997).

Kuttenn, F. and P. Mauvais-Jarvis, Intratumoral levels and metabolism of 4-hydroxytamoxifen after percutaneous administration at the breast level, C.R. Acad. Sci. III. 300: 457-462 (1985) (French).

Lee, K. H., B. A. Ward, Z. Desta, D. A. Flockhart and D. R. Jones, Quantification of tamoxifen and three metabolites in plasma by high-performance liquid chromatography with fluorescence detection: application to a clinical trial, J. Chromatogr. B. Analyt. Technol. Biomed. Life Sci., 791 (1-2): 245-53 (2003).

Malet C., A. Gompel, P. Spritzer, N Bricourt, N H Yaneva, I. Mowszowicz, F. Kutten and P Mauvais Jarvis, Tamoxifen and hydroxytamoxifen isomers versus estradiol effects on normal human breast cells in culture, Cancer Research, 48: 7193-7199 (1988).

Mauvais-Jarvis, P., N. Baudot, D. Castaigne, P. Banzet, and F. Kutterm, Trans-4-hydroxytamoxifen concentration and metabolism after local percutaneous administration to human breast, Cancer Research, 46:1521-1525 (1986).

Nishino, M. K. Hayakawa, Y. Nakamura, T. Morimoto and S. Mukaihara, Effects of tamoxifen on hepatic fat content and the development of hepatic steatosis in patients with breast cancer: high frequency of involvement and rapid reversal after completion of tamoxifen therapy, AJR Am. J. Roentgenol., 180(1): 129-34 (2003)

Pujol, H., J. Girault, P. Rouanet, S. Fournier, J. Grenier, J. Simony, J. B. Fourtillan, and J. L. Pujol, Phase 1 study of percutaneous 4-hydroxy-tamoxifen with analyses of 4-hydroxy-tamoxifen concentrations in breast cancer and normal breast tissue, Cancer Chemother. Pharmacol., 36:493-498 (1995).

Remington: The Science and Practice of Pharmacy, Alfonso R. Gennaro, Lippincott Williams & Wilkins, 2000, pp. 836-858.

Robertson and Katzenellenbogen, J. Org. Chem., 47: 2387 (1982).

Robertson, D. W., J. A. Katzenellenbogen, D. J. Long, E. A. Rorke and B. S. Katzenellenbogen, Tamoxifen antiestrogens. A comparison of the activity, pharmacokinetics, and metabolic activation of the cis and trans isomers of tamoxifen, J. Steroid Biochemistry, 16(1): 1-13 (1982).

Sauvez, F., D. Salin-Drouin, M. Attia, H. Bertheux, and R. Forster, Cutaneously applied 4-hydroxytamoxien is not carcinogenic in female rats. Carcinogenesis, 20: 843-50 (1999).

Shushan, A., T. Peretz, B. Uziely, A. Lewin and S. Mor-Yosef. Ovarian cysts in premenopausal and postmenopausal tamoxifen treated women with breast cancer, Am. J. Obstet. Gynecol., 174(1): 141-44 (1996).

Tan-Chiu, E., J. Wang, J. P. Costantino, S. Paik, C. Butch, D. L. Wicherham, B. Fisher and N. Wolmark, Effects of tamoxifen on benign breast disease in women at high risk for breast cancer, 95(4): 302-07 (2003).

Wijayaratne, A. L., S. C. Nagel, L. A. Paige, D. J. Christensen, J. D. Norris, D. M. Fowlkes, and D. P. McDonnell, Comparative Analyses of Mechanistic Difference among Anti-estrogens, Endocrinology, 140(12): 5828-5840 (1999).

What is claimed is:

1. A method of treating benign breast disease in a female patient, comprising percutaneously administering 4-hydroxy tamoxifen to a female patient having benign breast disease, wherein said 4-hydroxy tamoxifen is administered in a vehicle containing isopropyl myristate as a penetration enhancer.

2. A method according to claim 1, wherein about 0.25 to 2.0 mg/breast of said 4-hydroxy tamoxifen is administered to said patient per day.

3. A method according to claim 1, wherein said 4-hydroxy tamoxifen is formulated in a hydroalcoholic gel, a hydroalcoholic solution, a patch, an ointment, a cream, an emulsion (lotion), a powder or an oil.

4. A method according to claim 3, wherein said 4-hydroxy tamoxifen is formulated in a hydroalcoholic gel.

5. A method according to claim 3, wherein said 4-hydroxy tamoxifen is formulated in a hydroalcoholic composition containing a penetration enhancer, an aqueous vehicle, an alcoholic vehicle and a gelling agent.

6. A method according to claim 5, wherein said hydroalcoholic composition comprises a neutralizing agent.

7. A method according to claim 5, wherein said hydroalcoholic composition comprises:
   a) about 0.01% to 0.20% by weight of 4-hydroxy tamoxifen,
   b) about 0.5% to 2% by weight of isopropyl myristate,
   c) about 60% to 75% by weight of absolute alcohol,
   d) about 25% to 40% by weight of aqueous vehicle,
   e) about 0.5% to 5% by weight of gelling agent,
   wherein the percentage of components are weight to weight of the composition.

8. A method according to claim 7, wherein said alcohol is ethanol or isopropanol, and constitutes in absolute form about 60% to 75% by weight of the composition.

9. A method according to claim 7, wherein said aqueous vehicle is a phosphate buffered solution, and constitutes about 25% to 40% by weight of the composition.

10. A method according to claim 7, wherein said gelling agent is a polyacrylic acid or hydroxypropylcellulose, and constitutes about 0.5% to 5% by weight of the composition.

11. A method according to claim 7, wherein said hydroalcoholic composition further comprises a neutralizing agent selected in the group consisting of sodium hydroxide, ammonium hydroxide, potassium hydroxide, arginine, aminomethylpropanol, trolamine and tromethamine, which neutralizing agent exists at a neutralizing agent/gelling agent ratio between about 4:1 and 1:1.

12. A method according to claim 7, wherein said hydroalcoholic composition is packaged in a unit dose packet or in a multiple dose container with a metered pump.

13. A method according to claim 1, wherein said benign breast disease is a proliferative breast disease.

14. A method according to claim 13, wherein said proliferative breast disease is selected from the group consisting of adenosis, cysts, duct ectasia, fibroadenoma, fibrocystic disease, fibrosis, hyperplasia and metaplasia.

15. A method according to claim 14, wherein said patient is pre-menopausal.

16. A method according to claim 1, wherein said benign breast disease has an estrogen-related component.

* * * * *